United States Patent
Aksberg

(10) Patent No.: US 6,179,980 B1
(45) Date of Patent: Jan. 30, 2001

(54) CLAMP FOR ELECTROPHORESIS SYSTEMS

(75) Inventor: Arvi Aksberg, Lidingö (SE)

(73) Assignee: Amersham Pharmacia Biotech AB, Uppsala (SE)

(*) Notice: Under 35 U.S.C. 154(b), the term of this patent shall be extended for 0 days.

(21) Appl. No.: 09/043,556

(22) PCT Filed: Sep. 20, 1996

(86) PCT No.: PCT/SE96/01172

§ 371 Date: Mar. 23, 1998

§ 102(e) Date: Mar. 23, 1998

(87) PCT Pub. No.: WO97/12236

PCT Pub. Date: Apr. 3, 1997

(30) Foreign Application Priority Data

Sep. 25, 1995 (SE) .................................................. 9503312

(51) Int. Cl.$^7$ .................................................. G01N 27/26
(52) U.S. Cl. .................... 204/616; 204/618; 425/451.9
(58) Field of Search .................... 52/209.62, 204.69, 52/716.8; 24/462, 459, 563; 204/466, 467, 616, 618, 619, 620; 425/595, 451.9, 808

(56) References Cited

U.S. PATENT DOCUMENTS

| | | | |
|---|---|---|---|
| 3,256,577 | * 6/1966 | Bright | 24/563 |
| 4,035,377 | * 7/1977 | Detroy | 204/619 |
| 4,518,476 | 5/1985 | Delony et al. | 204/299 R |
| 4,817,253 | * 4/1989 | Harmatuik et al. | 24/458 |
| 4,820,398 | * 4/1989 | Yamato | 204/618 |
| 4,985,128 | * 1/1991 | Ebersole et al. | 204/469 |

* cited by examiner

Primary Examiner—Jill Warden
Assistant Examiner—Alex Noguerola
(74) Attorney, Agent, or Firm—Birch, Stewart, Kolasch & Birch, LLP

(57) ABSTRACT

A device in a gel slab assembly for an electrophoresis system having a gel enclosure which is defined by two plates which are spaced by at least two spacing strips, the device being provided with at least one clamp which is arranged to mutually clamp together the plates in the area of a spacing strip. In the device, each clamp is provided with a web portion and two shank portions. The shank portions include force exerting portions. The shank portions have such an extension that lines between force exerting portions pass through a spacing strip when the clamp is in a mounted position. The force exerting portion of one of the shank portions constitutes a hinge portion for cooperation with a groove-like recess in a supporting frame of the gel slab.

14 Claims, 3 Drawing Sheets

CLAMP FOR ELECTROPHORESIS SYSTEMS

This application is the national phase under 35 U.S.C. §371 of prior PCT International Application No. PCT/SE96/01172, which has an International filing date of Sep. 20, 1996, which designated the United States of America, the entire contents of which are hereby incorporated by reference.

BACKGROUND OF THE INVENTION

1. Field of the Invention

This invention concerns a device for use in electrophoresis.

2. Description of the Background Art

In an electrophoresis process a gel is subjected to a high electric tension on at least two sides. The applied tension results in migration of the molecules in the gel, a shorter or longer distance depending on, for example, the electric charge of the molecules. Hereby the movement direction of the molecules is always perpendicular to the equipotential lines, i.e. lines having the same potential in the gel. Totally decisive for a reliable result in respect of detection of separated molecules, is that the equipotential lines are straight and parallel, since otherwise erroneous detection occurs. Possible leaks from the gel enclosure thus result in electric contact between the gel and a liquid bath put under tension, resulting in sideward current leaks, curved equipotential lines and "curved migration" of molecules.

While forming the gel in the gel enclosure, it is further essential to obtain as homogeneous and even thick a gel as possible since also variations in the gel thickness result in undesired deviations from accurate equipotential line paths.

Known devices of the previously mentioned kind unfortunately suffer from the above discussed problems at a smaller or greater extent. As examples of devices which to date are used for clamping gel slab assemblies, those may be mentioned which clamp together the gel unit using screw fasteners, whereby a number of screw means which are distributed over the side edge are arranged to exert the desired pressing force. These previously known devices, however, have not satisfactory solved the problems in question, since an inherent adjustment variation exists because of the individually tightened screw means. This is also the case if the screws, as in certain cases, have been tightened with a torque indicator.

Another known device is applied by two jaw portions being pressed over the edge of the gel assembly by means of an eccentric mechanism. Also this device, however, suffers from problems related to exerting even pressure. A further problem is that of sideward movement, which may occur in connection with the tightening of the eccentric, and which may result in an undesired mutual sideward movement between the glass plates which are parts of the assembly. A further problem is insufficient clamping force, which results in the above discussed sideward leakage, particularly when forming the gel.

U.S. Pat. No. 4,035,377 concerns a slab gel electrophoresis apparatus having clamps of the paper clamp type for holding the plates together. The lengths of the clamping portions are such that an untrained person by mistake can apply the clamping force inside the spacing strips. The clamps are applied by a lateral movement over the plates, leading to possibility of inexact positioning and force distribution. The large dimensions of the clamps makes it necessary to remove some of them when carrying out the electrophoresis process.

SUMMARY OF THE INVENTION

It is an object of this invention to provide a device which solves the above discussed problems in a simple, reliable, space saving and cost effective manner.

In this way, a device is provided that is simple to manufacture, that may be applied also by untrained personnel and still achieve accurately directed clamping force of a desired magnitude. It is further assured that pressing is exerted within the width of a spacing strip, which is essential, since pressure on the non-conductive transparent plates beside a spacing strip, i.e. over the actual gel enclosure, results in a bending movement on at least one of the plates and thus an undesired deformation of the gel enclosure. By the clamping means being dimensioned to deliver the desired clamping force in the applied position, problems related to erroneous tightening, unevenness, etc. are avoided. The exact clamping force to be exerted is easily tested by a person skilled in the art.

Different materials may be used for the clamping means. Stainless steel is preferred but also other metals may come into question as well as certain synthetic materials, particularly reinforced ones, such as so-called construction plastic materials.

The feature that one of the shank portions constitutes a hinge portion for cooperation with a groove-like recess in a supporting frame of the gel slab assembly, simplified orientation and mounting of the clamping means, particularly in electrophoresis systems according to the state of the art where the frame is provided with a groove-like recess.

It should be noted that this invention concerns continuous detection during the migration of the molecules in an equipment using laser-beams in as thin a gel slab as possible, typically 0.3–0.5 mm, which raises far stricter demands with respect to tightness of the assembly. This because of curved migration being even more critical in thin gel slabs. Leaks due to uneven force distribution result in curved equipotential lines and may lead to poor results. This is accentuated in an electrophoresis system relating to this invention.

The invention brings about the possibility of simplified manufacture of the clamping means using in per se known, conventional methods. Plate material means initially slab or band shaped metal material, and as indicated above, stainless steel is preferred.

The invention provides further facilitated handling and ensures that a necessary clamping force is safely obtained which is distributed along the edge of the assembly. In this way the risk of applying a wrong number of clamping means onto the assembly is eliminated.

The invention also concerns electrophoresis systems. Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention is now described in greater detail in the light of embodiments and with reference to the annexed drawings, wherein.

DETAILED DESCRIPTION

Figure 1:
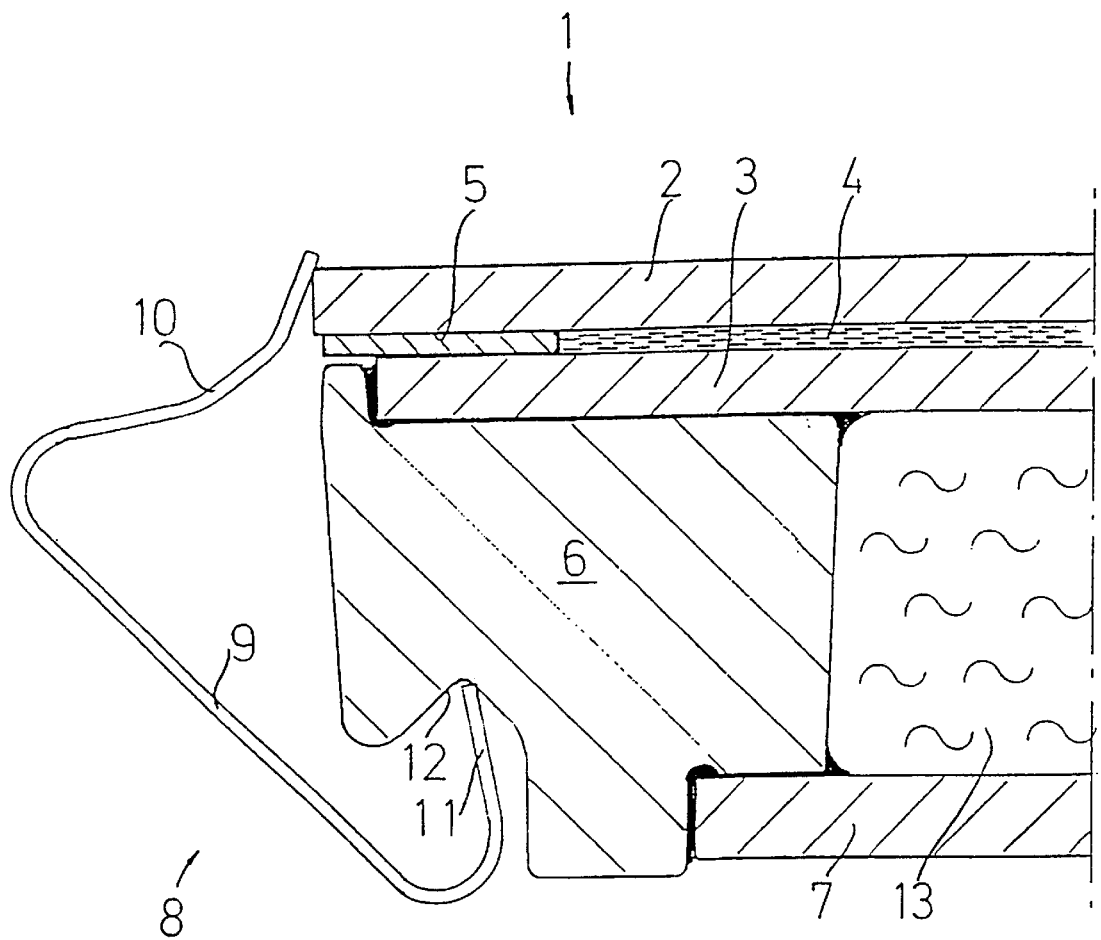
FIG. 1 shows a device according to the invention with a gel slab assembly for an electrophoresis system in an entering position.

FIG. 1 shows a detail of a section of a gel slab assembly 1 including glass plates 2 and 3 which are separated by spacing strips (one is shown at 5), made of glass or any other suitable material, in order to obtain a gel enclosure 4. It should be noted that the plates 2, 3 do not have to be of glass, and that also other materials may be used in different applications, as long as the plates are electrically non-conductive and transparent. An example of another possible material is plexiglass.

Figure 2:
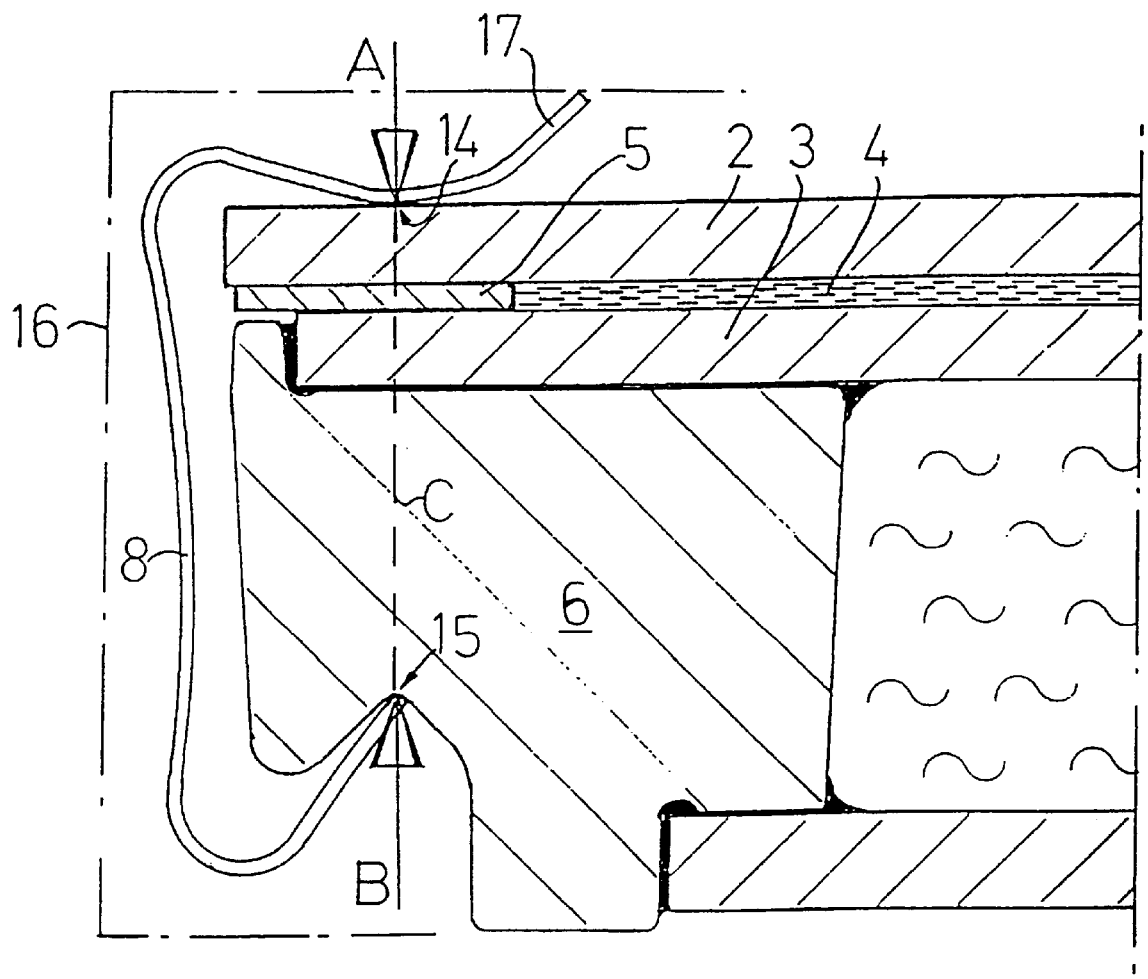
FIG. 2 shows the device with the clamping means in an applied position.

The glass plates 2, 3 in this case rest on a frame, a profile 6 of which is shown in FIGS. 1 and 2. The frame together with the inner glass plate 3 and a cover plate 7 defines an enclosure 13 for tempering liquid.

In order to clamp together the plate assembly according to the invention, a clamping means 8 is used. The clamping 8 is means constituted of a plate profile having a central web portion 9, a first shank portion 10 and a second shank portion 11 which are directed such that they are able to exert a clamping force onto an intermediate item. FIG. 1 shows the clamping means 8 in an entering position whereby the second shank portion 11 engages a groove 12 in the frame profile 6.

FIG. 2 shows the clamping means 8 in a mounted position, whereby it is clear that the shank portions have such an extension that the line C between press exerting portions 14 and 15 on the respective shank portions pass through the spacing strip 5. This results in the above discussed advantages. The forces from the respective press exerting portions are indicated with arrows A and B, whereby it is also to be understood that the clamp, as a result from the low friction between metal and glass, will occupy and place itself in a position resulting in a force that is perpendicular to the glass, and thus no possible sideward forces which could lead to sliding between the glasses. On FIG. 2 the interrupted line 16 indicates the relatively small space inside the electrophoresis instrument that is consumed for containing the clamping means 8.

Figure 3:
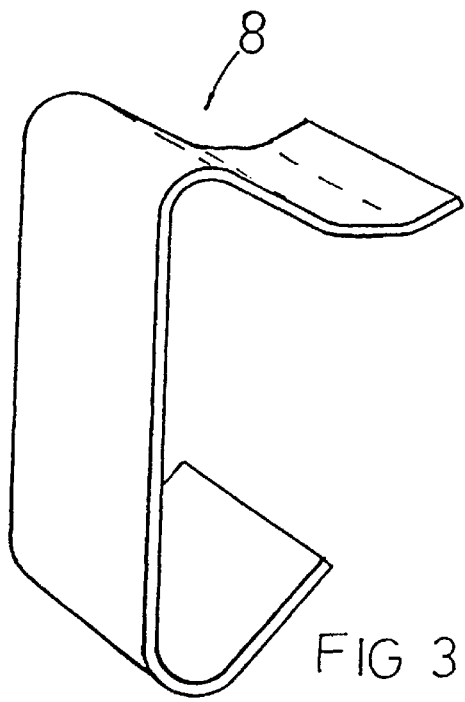
FIG. 3 shows the clamping means of FIGS. 1 and 2 in a perspective view.

FIG. 3 shows the clamping means 8 in a perspective view and in this connection it could be mentioned that the described construction makes it easy to adjust the force to be exerted in a number of ways, namely by variation of number of clamps, variation of clamp width and by altering the material thickness. Also the geometry with respect to other aspects of the clamping means may differ from what is shown in the figures, whereby in certain cases, when the frame 6 is eliminated from the gel slab assembly, the clamping means may be provided with two essentially identical shank portions, which in that case have a shape essentially according to item 10 in FIG. 1. The outer part of the first shank portion 10 (17 in FIG. 2) is preferably bent upwards to make it possible, in a simple way, to remove it after the completed electrophoresis process.

Figure 4:
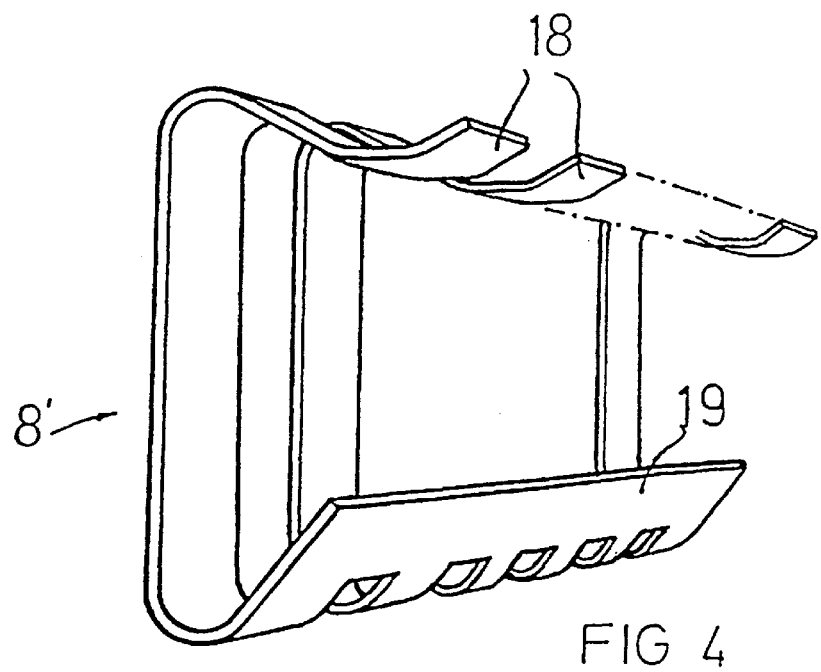
FIG. 4 shows an alternative embodiment of the clamping means.

FIG. 4 shows an embodiment of the clamping means 8' which is provided with a number of sidewardly separated but joined clamping elements 18. This embodiment brings about the advantages that make possible a sequential snapping-on of the different clamping elements when mounting. In this embodiment a joining connecting element 19 is arranged in the outer area of the second shank portion but the joining function may also be accomplished by connecting elements being arranged otherwise. What is important here is that the connecting element do not have such a stiffness or extension that the straightness of the glass plates and thereby that of the gel is affected along the edge. A clamping means having generally an unchanged section along essentially the whole length of the edge of the assembly is, however, within the scope of the invention. It is hereby essential that the clamping means 8' is provided with notches for different gel assembly connections, for example for laser beam transmission.

A further advantage with a device according to the invention is that the clamping means has proved to have the quality to take up considerable variations in tolerances as well as a chosen change of thickness of the elements that are intended to be clamped together. The same clamping means is thus usable with a spacing strip thickness of 0.3 mm as well as 0.5 mm. The chosen solution also solves a problem which appears when the gel is formed in vacuum (more correctly a strong under-pressure) or suction with the support of capillary power, whereby vacuum will appear at the suction stage, since then the glasses are essentially bent inwards towards the gel enclosure prior to the gel being completely sucked in. The solution according to the invention will compensate for this change of form of the glasses in a flexible way without the occurrence of any sliding movements. Further advantages are that it is a robust and easily used construction which principally may not be applied wrongly, that it is easily cleaned and easily made chemically resistant.

The invention being thus described, it will be obvious that the same may be varied in many ways. Such variations are not to be regarded as a departure from the spirit and scope of the invention, and all such modifications as would be obvious to one skilled in the art were intended to be included within the scope of the following claims.

What is claimed is:

1. A device in a gel slab assembly for an electrophoresis system comprising:

a gel enclosure which is defined by two electrically non-conductive, transparent, plane and parallel plates which are spaced by at least two spacing strips being arranged at two edges;

at least one clamping means which is arranged so as to mutually clamp together the plates in the area of a spacing strip, each clamping means being produced from a resilient material and being provided with a web portion and two shank portions, said shank portions including force exerting portions which are facing each other, the clamping means being dimensioned so as to exert an adjusted clamping force in a mounted position, wherein the shank portions have such an extension that lines between the force exerting portions safely pass through a spacing strip when the clamping means is in a mounted position, and wherein the force exerting portion of one of the shank portions constitutes a hinge portion for cooperation with a grooved recess in a supporting frame of the gel slab assembly.

2. The device according to claim 1, wherein the clamping means is produced from plate metal.

3. The device according to any one of claims 1–2, wherein the clamping means has a sideward length which is adapted with respect to the edge length of the gel slab assembly so that the desired clamping function is accomplished with one single clamping means.

4. The device according to any one of claims 1–2 wherein the clamping means is constituted of at least two sidewardly joined clamping elements forming one unit.

5. An electrophoresis system including at least one device according to any one of claims 1–2.

6. The system according to claim 5, wherein said system is utilized for the analysis of nucleic acids, proteins or peptides.

7. The system according to claim 5, wherein said system is utilized for automatic DNA or RNA analysis.

8. A gel slab assembly for an electrophoresis system comprising:

a gel enclosure including two electrically non-conductive, transparent, plane and parallel plates;

at least two spacing strips arranged along side edges of said plates for spacing apart said plates;

a supporting frame for supporting said gel enclosure, said supporting frame having a groove in a rear surface thereof;

at least one clamp located along one of said side edges of said plates, said clamp arranged to mutually clamp together said plates in an area of said spacing strips, each clamp formed of a resilient material, said clamp including:

a first shank portion, a second shank portion, and a web portion extending therebetween, said first shank portion and said second shank portion being shaped differently from one another, each of said shank portions including force exerting portions facing each other, said force exerting portion of said first shank portion comprising a hinge portion receivable is said groove of said supporting frame, said force exerting portion of said second shank portion comprising a sliding portion, said clamp being pivotable about said hinge portion received in said groove so that said sliding portion of said second shank portion may slide onto one of said plates and into a mounted position, wherein a line extending between the force exerting portions of said clamp passes through one of said spacing strips when said clamp is in said mounted position.

9. The gel slab assembly according to claim 8, wherein said clamp is produced from plate metal.

10. The gel slab assembly according to claim 8, wherein said clamp has a length with respect to the edge length of the gel slab assembly so that a desired clamping function is accomplished with one clamp per side of said gel slab assembly.

11. The gel slab assembly according to claim 8, wherein said clamp includes a plurality of second shank portions and web portions joined together at said first shank portion.

12. The gel slab assembly according to claim 8, wherein said second shank portion includes an upwardly bent portion at an end thereof.

13. The gel slab assembly according to claim 12, wherein said sliding portion of said second shank portion is located between said web and said upwardly bent portion.

14. The gel slab assembly according to claim 8, wherein said first shank portion includes a straight portion extending along a line oriented approximately 35 degrees with respect to a line extending along said web.

* * * * *